(12) United States Patent
Trah et al.

(10) Patent No.: US 8,658,644 B2
(45) Date of Patent: Feb. 25, 2014

(54) PYRIDAZINE DERIVATIVES, PROCESSES FOR THEIR PREPARATION AND THEIR USE AS FUNGICIDES

(75) Inventors: Stephan Trah, Stein (CH); Clemens Lamberth, Stein (DE)

(73) Assignee: Syngenta Crop Protection, LLC, Greensboro, NC (US)

( * ) Notice: Subject to any disclaimer, the term of this patent is extended or adjusted under 35 U.S.C. 154(b) by 59 days.

(21) Appl. No.: 13/576,945

(22) PCT Filed: Feb. 1, 2011

(86) PCT No.: PCT/EP2011/051341
§ 371 (c)(1),
(2), (4) Date: Aug. 3, 2012

(87) PCT Pub. No.: WO2011/095461
PCT Pub. Date: Aug. 11, 2011

(65) Prior Publication Data
US 2012/0295876 A1    Nov. 22, 2012

(51) Int. Cl.
*C07D 237/08* (2006.01)
*C07D 237/12* (2006.01)
*C07D 237/14* (2006.01)
*A61K 31/50* (2006.01)

(52) U.S. Cl.
USPC ............ 514/247; 544/224; 544/239; 544/241

(58) Field of Classification Search
USPC .......................... 544/224, 239, 241; 514/247
See application file for complete search history.

(56) References Cited

U.S. PATENT DOCUMENTS

| 8,338,604 B2 * | 12/2012 | Hynes et al. ................. 546/121 |
| 2012/0135995 A1 * | 5/2012 | Sharpe ......................... 514/247 |

FOREIGN PATENT DOCUMENTS

| EP | 1767529 | 3/2007 |
| WO | 2008/089934 | 7/2008 |
| WO | WO 2008089934 A1 * | 7/2008 |

* cited by examiner

*Primary Examiner* — James O Wilson
*Assistant Examiner* — Oluwafemi Masha
(74) *Attorney, Agent, or Firm* — R. Kody Jones

(57) ABSTRACT

The present invention relates to novel pyridazine derivatives of formula (I) wherein $R^1$ is methyl or ethyl; $R^2$ is H or chloro; $R^3$ is fluoro or chloro; $R^4$ is fluoro or methoxy; and $R^5$ is chloro or methoxy or an agrochemically usable salt from thereof, as active ingredients which have microbiodidal activity, in particular fungicidal activity.

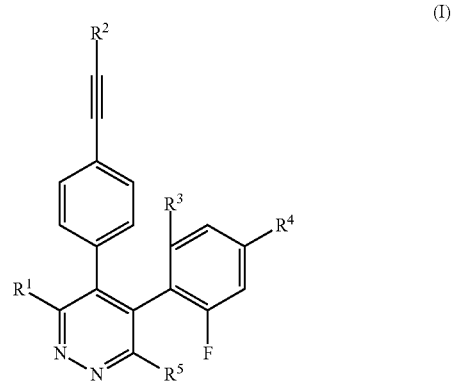

(I)

12 Claims, No Drawings

PYRIDAZINE DERIVATIVES, PROCESSES FOR THEIR PREPARATION AND THEIR USE AS FUNGICIDES

This application is a 371 of International Application No. PCT/EP2011/051341 filed Feb. 1, 1011, which claims priority to EP 10152669.7 filed Feb. 4, 2010, the contents of which are incorporated herein by reference.

The present invention relates to novel pyridazine derivatives having microbiocidal activity, in particular, fungicidal activity, to processes and intermediates for preparing them, to agricultural compositions comprising them and to methods of using the compounds or compositions in agriculture or horticulture for controlling or preventing infestation of plants, harvested food crops, seeds or non-living materials by phytopathogenic microorganisms, preferably fungi.

Pyridazine derivatives having fungicidal activity are disclosed in international patent applications WO2005121104, WO2006001175, WO2007066601, WO2007080720, WO2008009405, WO2008009406 and WO2008049585. There exists a need for alternative methods of control of fungi. Preferably, new compounds may possess improved fungicidal properties, such as improved efficacy, improved selectivity, lower tendency to generate resistance or activity against a broader spectrum of fungi. Compounds may be more advantageously formulated or provide more efficient delivery and retention at sites of action, or may be more readily biodegradable. In particular there exists a need for fungicides having an improved curative action.

It has surprisingly been found that the pyridazine compounds of the present invention exhibit unexpected fungicidal activity, including unexpected curative activity, and are therefore suitable for use in agriculture as crop protection agents to combat or prevent fungal infestations.

The present invention provides a compound of formula (I)

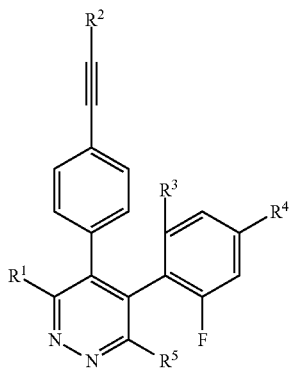

(I)

wherein
$R^1$ is methyl or ethyl;
$R^2$ is H or chloro;
$R^3$ is fluoro or chloro;
$R^4$ is fluoro or methoxy; and
$R^5$ is chloro or methoxy;
or an agrochemically usable salt form thereof.

The present invention includes all those possible isomeric forms and mixtures thereof for a compound of formula (I). For instance, atropisomers may occur as a result of restricted rotation about a single bond.

In a preferred embodiment:
$R^1$ is methyl;
$R^2$ is H or chloro;
$R^3$ is fluoro;
$R^4$ is fluoro or methoxy; and
$R^5$ is chloro or methoxy.

In a more preferred embodiment:
$R^1$ is methyl;
$R^2$ is H;
$R^3$ is fluoro;
$R^4$ is fluoro or methoxy; and
$R^5$ is chloro.

Preferred individual compounds are selected from
3-chloro-5-(4-ethynylphenyl)-6-methyl-4-(2,4,6-trifluorophenyl)pyridazine;
3-chloro-4-(2,6-difluoro-4-methoxyphenyl)-5-(4-ethynylphenyl)-6-methylpyridazine;
4-(2,6-difluoro-4-methoxyphenyl)-5-(4-ethynylphenyl)-3-methoxy-6-methylpyridazine;
4-(4-ethynylphenyl)-6-methoxy-3-methyl-5-(2,4,6-trifluorophenyl)pyridazine;
3-chloro-5-(4-chloroethynylphenyl)-6-methyl-4-(2,4,6-trifluorophenyl)pyridazine; and
3-chloro-5-(4-chloroethynylphenyl)-4-(2,6-difluoro-4-methoxyphenyl)-6-methyl-pyridazine.

The compounds according to the present invention can be prepared according to the following reaction schemes, in which, unless otherwise stated, the definition of each variable $R^1$, $R^2$, $R^3$ and $R^4$ are as defined above for a compound of formula (I).

The compounds of formula (I.2) may be obtained by transformation of a compound of formula (I.1) with methanol and base or with sodium methoxide.

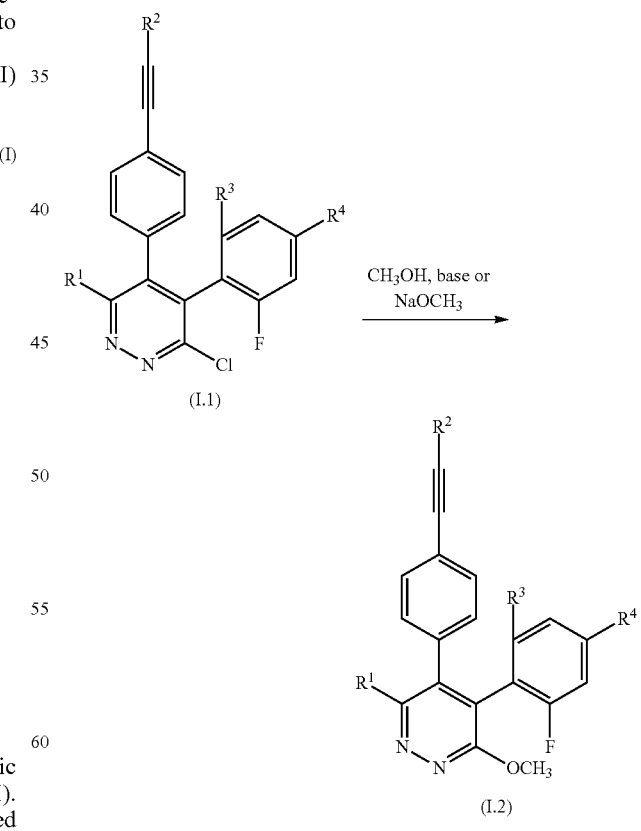

The compounds of formula (I.1) may be obtained by transformation of a compound of formula (I.3) with phosphorus oxychloride or thionyl chloride.

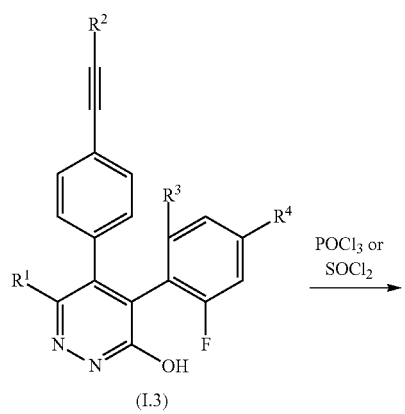

(I.3)

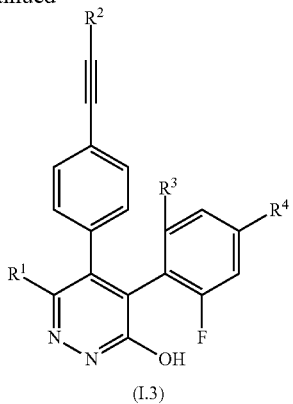

(I.3)

The compounds of formula (II) may be obtained by transformation of a compound of formula (III) by oxidation with oxygen, air or 3-chloroperbenzoic acid.

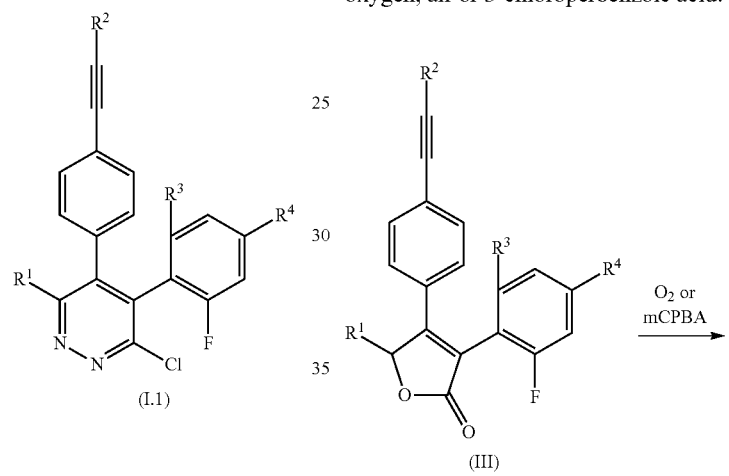

The compounds of formula (I.3) may be obtained by transformation of a compound of formula (II) with a hydrazine derivative, e.g. hydrazine hydrate.

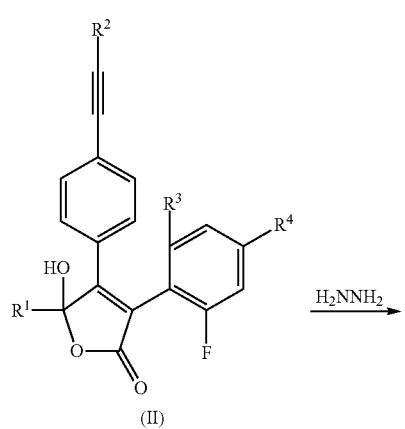

(II)

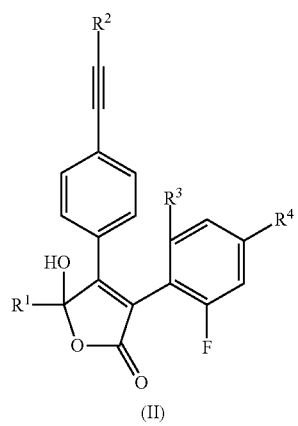

(II)

The compounds of formula (III) may be obtained by transformation of a compound of formula (IV), wherein $R^1$, $R^2$, $R^3$ and $R^4$ are as defined for formula (I), with a base, e.g. pyridine, triethylamine, diisopropylethylamine, 1,5-diazabicyclo[4.3.0]non-5-ene or 1,8-diazabicyclo[5.4.0]undec-7-ene.

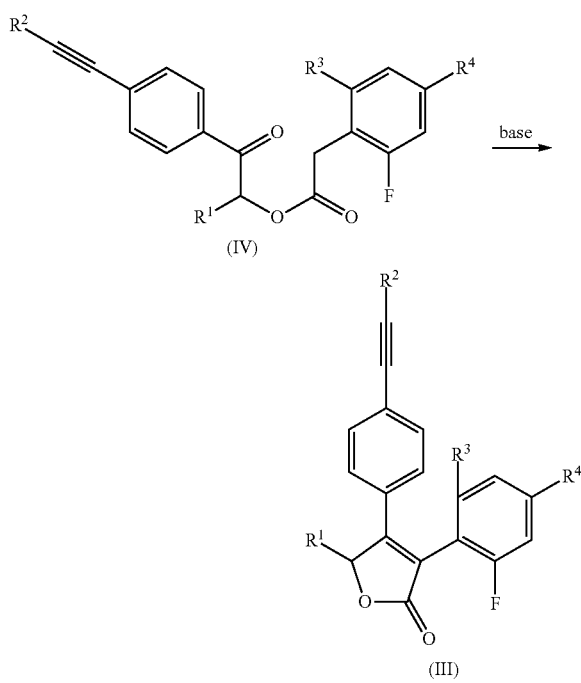

(IV)

(III)

The compounds of formula (IV) may be obtained by transformation of a compound of formula (V), wherein Hal is halogen, preferably chlorine or bromine, with a compound of formula (VI) and a base, e.g. pyridine, triethylamine, diisopropylethylamine, 1,5-diazabicyclo[4.3.0]non-5-ene or 1,8-diazabicyclo[5.4.0]undec-7-ene.

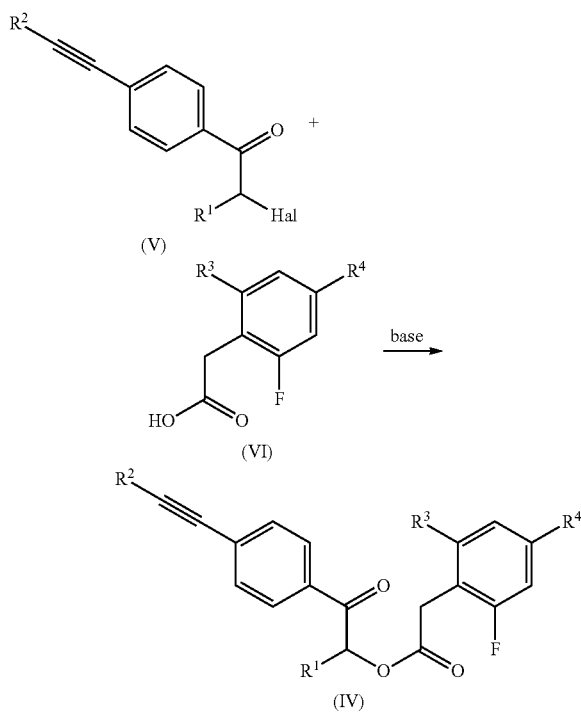

(V)

(VI)

(IV)

The compounds of formula (I.3), (II), (III) and (IV) form additional aspects of the present invention.

The compounds of formula (I) can be used in unmodified form or, preferably, together with carriers and adjuvants conventionally employed in the art of formulation.

Therefore the invention additionally provides compositions for controlling and protecting against phytopathogenic micro-organisms, comprising a compound of formula (I) and an inert carrier, and to a method of controlling or preventing infestation of useful plants by phytopathogenic micro-organisms, wherein a composition, comprising a compound of formula (I) as active ingredient and an inert carrier, is applied to the plants, to parts thereof or the locus thereof.

In addition, the invention could be used to protect non-living materials from fungal attack, e.g. lumber, wall boards and paint.

To this end compounds of formula (I) and inert carriers are conveniently formulated in known manner to mollifiable concentrates, coat able pastes, directly spray able or dilatable solutions, dilute emulsions, wet table powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or pacifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO199733890.

The compounds of formula (I) or compositions, comprising a compound of formula (I) as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides, plant growth regulators as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula (I), or a composition, comprising a compound of formula (I) as active ingredient and an inert carrier, is foliar application. The frequency of application and the rate of application will depend on the risk of infestation by the corresponding pathogen. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, i.e. a composition comprising the compound of formula (I) and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula (I), 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

The invention relates to a method of controlling or preventing infestation of useful plants by phytopathogenic micro-organisms, wherein a compound of formula (I) is applied as active ingredient to the plants, to parts thereof or the locus thereof. The compounds of formula (I) according to the invention are distinguished by excellent activity at low rates of application, by being well tolerated by plants and by being environmentally safe. They have very useful curative, preventive and systemic properties and are used for protecting numerous useful plants. The compounds of formula (I) can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic micro-organisms.

It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula (I) according to the invention may be used for controlling fungi in related areas, for example in the protection of technical materials, including wood and wood related technical products, in food storage or in hygiene management.

Within the scope of the invention, useful plants to be protected typically comprise the following groups of plants: cereals (wheat, barley, rye, oat, rice, maize, sorghum and related species); beets (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucurbit plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The term "useful plants" and/or "target crops" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" and/or "target crops" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" and/or "target crops" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula (I) are, for example, effective against the phytopathogenic fungi of the following classes: The compounds of formula (I) are, for example, effective against the phytopathogenic fungi of the following classes: Fungi imperfecti (e.g. *Alternaria* spp.), Basidiomycetes (e.g. *Corticium* spp., *Ceratobasidium* spp., *Waitea* spp., *Thanatephorus* spp., *Rhizoctonia* spp., *Hemileia* spp., *Puccinia* spp., *Phakopsora* spp., *Ustilago* spp., *Tilletia* spp.), Ascomycetes (e.g. *Venturia* spp., *Blumeria* spp., *Erysiphe* spp., *Podosphaera* spp., *Uncinula* spp., *Monilinia* spp., *Sclerotinia* spp., *Colletotrichum* spp., *Glomerella* spp., *Fusarium* spp., *Gibberella* spp., *Monographella* spp., *Phaeosphaeria* spp., *Mycosphaerella* spp., *Cercospora* spp., *Pyrenophora* spp., *Rhynchosporium* spp., *Magnaporthe* spp., *Gaeumannomyces* spp., *Oculimacula* spp., *Ramularia* spp., *Botryotinia* spp.) and Oomycetes (e.g. *Phytophthora* spp., *Pythium* spp., *Plasmopara* spp., *Peronospora* spp., *Pseudoperonospora* spp. *Bremia* spp). Outstanding activity has been observed against powdery mildews (e.g. *Uncinula necator*), rusts (e.g. *Puccinia* spp.) and leaf spots (e.g. *Mycosphaerella* spp.). Furthermore, the novel compounds of formula (I) are effective against phytopathogenic gram negative and gram positive bacteria (e.g. *Xanthomonas* spp, *Pseudomonas* spp, *Erwinia amylovora, Ralstonia* spp.) and viruses (e.g. tobacco mosaic virus).

In a preferred embodiment of the invention, the compounds and compositions of the present invention are used against the fungal organism *Mycosphaerella graminicola*.

The compounds of formula (I) are normally used in the form of fungicidal compositions for controlling or protecting against phytopathogenic microorganisms, comprising as active ingredient at least one compound of formula (I) or at least one preferred individual compound as above-defined, in free form or in agrochemically usable salt form, and at least one of the above-mentioned adjuvants.

Said fungicidal compositions for controlling or protecting against phytopathogenic microorganisms, comprising as active ingredient at least one compound of formula (I) or at least one preferred individual compound as above-defined, in free form or in agrochemically usable salt form, and at least one of the above-mentioned adjuvants can be mixed with other fungicides, resulting in some cases in unexpected synergistic activities.

The present invention relates additionally to mixtures comprising at least a compound of formula I and at least a further, other biocidally active ingredient and optionally further ingredients. The further, other biocidally active ingredient are known for example from "The Pesticide Manual" [The Pesticide Manual—A World Compendium; Thirteenth Edition (New edition (2 Nov. 2003)); Editor: C. D. S. Tomlin; The British Crop Protection Council, ISBN-10: 1901396134; ISBN-13: 978-1901396133] or its electronic version "e-Pesticide Manual V4.2" or from the website http://www.alanwood.net/pesticides/ or preferably one of the further pesticides listed below.

The following mixtures of the compounds of TX with a further active ingredient (B) are preferred (the abbreviation "TX" means "one compound selected from the group consisting of the compounds of Tables 1 of the present invention, thus the abbreviation "TX" means at least one compound selected from the compounds Compound No. 1 to Compound No. 17:

(B)
(B1) a strobilurin fungicide+TX,
(B2) an azole fungicide+TX,
(B3) a morpholine fungicide+TX,
(B4) an anilinopyrimidine fungicide+TX,
(B5) a fungicide selected from the group consisting of
Anilazine+TX, arsenates+TX, benalaxyl+TX, benalaxyl-M+TX, benodanil+TX, benomyl+TX, benthiavalicarb+TX, benthiavalicarb-isopropyl+TX, biphenyl+TX, bitertanol+TX, blasticidin-S+TX, bordeaux mixture+TX, boscalid+TX, bupirimate+TX, cadmium chloride+TX, captafol+TX, captan+TX, carbendazim+TX, carbon disulfide+TX, carboxin+TX, carpropamid+TX, cedar leaf oil+TX, chinomethionat+TX, chlorine+TX, chloroneb+TX, chlorothalonil+TX, chlozolinate+TX, cinnamaldehyde+TX, copper+TX, copper ammoniumcarbonate+TX, copper hydroxide+TX, copper octanoate+TX, copper oleate+TX, copper sulphate+TX, cyazofamid+TX, cycloheximide+TX, cymoxanil+TX, dichlofluanid+TX, dichlone+TX, dichloropropene+TX, diclocymet+TX, diclomezine+TX, dicloran+TX, diethofencarb+TX, diflumetorim+TX, dimethirimol+TX, dimethomorph+TX, dinocap+TX, dithianon+TX, dodine+TX, edifenphos+TX, ethaboxam+TX, ethirimol+TX, etridiazole+TX, famoxadone+TX, fenamidone+TX, fenaminosulf+TX, fenamiphos+TX, fenarimol+TX, fenfuram+TX, fenhexamid+TX, fenoxanil+TX, fenpiclonil+TX, fentin acetate+TX, fentin chloride+TX, fentin hydroxide+TX, ferbam+TX, ferimzone+TX, fluazinam+TX, fludioxonil+TX, flusulfamide+TX, flusulfamide+TX, flutolanil+TX, folpet+TX, formaldehyde+TX, fosetyl-aluminium+TX, fthalide+TX, fuberidazole+TX, furalaxyl+TX, furametpyr+TX, flyodin+TX, fuazatine+TX, hexachlorobenzene+TX, hymexazole+TX, iminoctadine+TX, iodocarb+TX, iprobenfos+TX, iprodione+TX, iprovalicarb+TX, isoprothiolane+TX, kasugamycin+TX, mancozeb+TX, maneb+TX, manganous dimethyldithiocarbamate+TX, mefenoxam+TX, mepronil+TX, mercuric chloride+TX, mercury+TX, metalaxyl+TX, methasulfocarb+TX, metiram+TX, metrafenone+TX, nabam+TX, neem oil (hydrophobic extract)+TX, nuarimol+TX, octhilinone+TX, ofurace+TX, oxadixyl+TX, oxine copper+TX, oxolinic acid+TX, oxycarboxin+TX, oxytetracycline+TX, paclobutrazole+TX, paraffin oil+TX, paraformaldehyde+TX, pencycuron+TX, pentachloronitrobenzene+TX, pentachlorophenol+TX, penthiopyrad+TX, perfurazoate+TX, phosphoric acid+TX, polyoxin+TX, polyoxin D zinc salt+TX, potassium bicarbonate+TX, probenazole+TX, procymidone+TX, propamocarb+TX, propineb+TX, proquinazid+TX, prothiocarb+TX, pyrazophos+TX, pyrifenox+TX, pyroquilon+TX, quinoxyfen+TX, quintozene+TX, silthiofam+TX, sodium bicarbonate+TX, sodium diacetate+TX, sodium propionate+TX, streptomycin+TX, sulphur+TX, TCMTB+TX, tecloftalam+TX, tecnazene+TX, thiabendazole+TX, thifluzamide+TX, thiophanate+TX, thiophanate-methyl+TX, thiram+TX, tolclofos-methyl+TX, tolyfluanid+TX, triazoxide+TX, trichoderma harzianum+TX, tricyclazole+TX, triforine+TX, triphenyltin hydroxide+TX, validamycin+TX, vinclozolin+TX, zineb+TX, ziram+TX, zoxamide+TX, 1+TX, 1-bis(4-chlorophenyl)-2-ethoxyethanol+TX, 2+TX, 4-dichlorophenyl benzenesulfonate+TX, 2-fluoro-N-methyl-N-1-naphthylacetamide+TX, 4-chlorophenyl phenyl sulfone+TX, a compound of formula B-5.1+TX (B-5.1)

a compound of formula B-5.2+TX (B-5.2)

a compound of formula B-5.3+TX

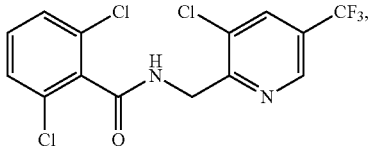

(B-5.3)

a compound of formula B-5.4+TX

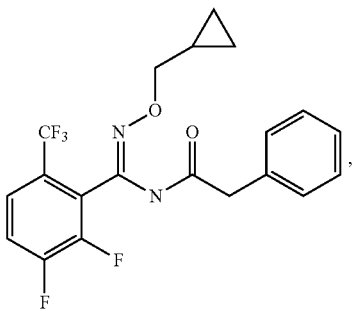

(B-5.4)

a compound of formula B-5.5+TX

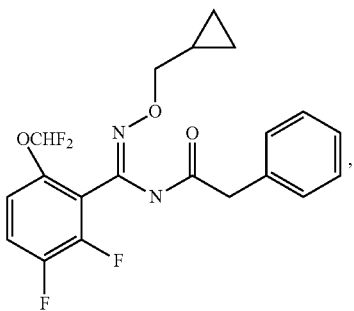

(B-5.5)

a compound of formula B-5.6+TX

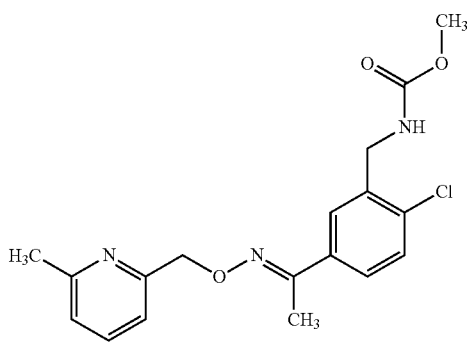

(B-5.6)

a compound of formula B-5.7+TX

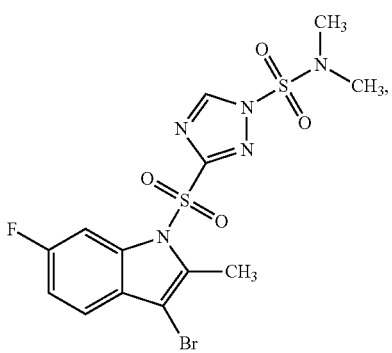

(B-5.7)

3-difluoromethyl-1-methyl-1H-pyrazole-4-carboxylic acid (2-bicyclopropyl-2-yl-phenyl)-amide (compound B-5.8)+TX, 3-difluoromethyl-1-methyl-1H-pyrazole-4-carboxylic acid (9-isopropyp-1,2,3,4-tetrahydro-1,4-methano-naphthalen-5-yl)-amide (compound B-5.9)+TX, 1,3-dimethyl-5-fluoro-1H-pyrazole-4-carboxylic acid [2-(1,3-dimethylbutyl)phenyl]-amide (compound B-5.10)+TX, 3-difluoromethyl-1-methyl-1H-pyrazole-4-carboxylic acid (3',4'-dichloro-5-fluoro-1,1'-biphenyl-2-yl)-amide (compound B-5.11)+TX, N-{2-[3-chloro-5-(trifluoromethyl)pyridin-2-yl]ethyl}-2-(trifluoromethyl)benzamid (compound B-5.12)+TX, 3-difluoromethyl-1-methyl-1H-pyrazole-4-carboxylic acid N-[2-(1,1,2,2-tetrafluoroethoxy)phenyl]-amide (compound B-5.13)+TX, 3-difluoromethyl-1-methyl-1H-pyrazole-4-carboxylic acid N-[2-(1,1,2,3,3,3-hexafluoropropoxy)phenyl]-amide (compound B-5.14), 3-difluoromethyl-1-methyl-1H-pyrazole-4-carboxylic acid N-[2-(2-chloro-1+TX, 1,2-trifluoroethoxy)phenyl]-amide (compound B-5.15)+TX, 3-difluoromethyl-1-methyl-1H-pyrazole-4-carboxylic acid N-(4'-trifluoromethyl-biphen-2-yl)-amide (compound B-5.16)+TX, 3-difluoromethyl-1-methyl-1H-pyrazole-4-carboxylic acid N-(2'-trifluoromethyl-biphen-2-yl)-amide (compound B-5.17) and 3-difluoromethyl-1-methyl-1H-pyrazole-4-carboxylic acid N-(2'-trifluoromethyl-biphen-2-yl)-amide (compound B-5.18)+TX; (B6) a plant-bioregulator selected from the group consisting of acibenzolar-5-methyl+TX, chlormequat chloride+TX, ethephon+TX, mepiquat chloride and trinexapc-ethyl;
(B7) an insecticide selected from the group consisting of abamectin+TX, clothianidin+TX, emamectin benzoate+TX, imidacloprid+TX, tefluthrin+TX, thiamethoxam+TX, and a compound of formula IV+TX

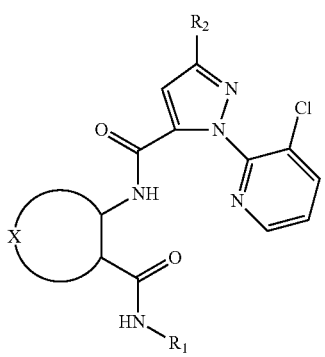

(IV)

wherein X is a bivalent group selected from

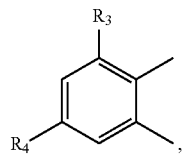 (X₁)

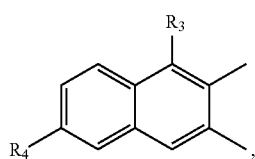 (X₂)

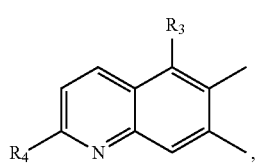 (X₃)

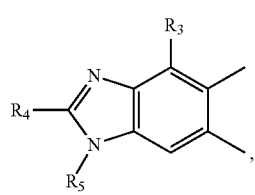 (X₄)

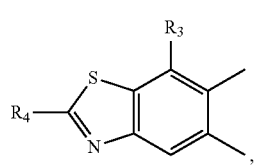 (X₅)

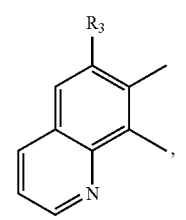 (X₆)

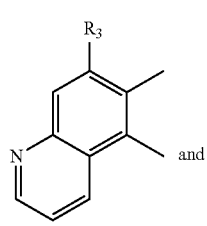 and (X₇)

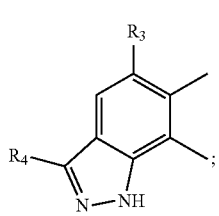 (X₈)

wherein
a) $R_1$ is cyclopropyl substituted by cyclopropyl at the 1-position, $R_2$ is bromine, $R_3$ is methyl, $R_4$ is CN and X is $X_1$;
b) $R_1$ is methyl substituted by cyclopropyl, $R_2$ is $CF_3$, $R_3$ is methyl, $R_4$ is Cl and X is $X_1$;
c) $R_1$ is cyclopropyl substituted by cyclopropyl at the 1-position, $R_2$ is $CF_3$, $R_3$ is methyl, $R_4$ is Cl and X is $X_1$;
d) $R_1$ is cyclopropyl substituted by cyclopropyl at the 1-position, $R_2$ is $CF_3$, $R_3$ is methyl, $R_4$ is CN and X is $X_1$;
e) $R_1$ is cyclopropyl substituted by cyclopropyl at the 1-position, $R_2$ is $OCH_2CF_3$, $R_3$ is methyl, $R_4$ is CN and X is $X_1$;
f) $R_1$ is isopropyl, $R_2$ is methoxy; $R_3$ is methyl, $R_4$ is hydrogen and X is $X_8$;
g) $R_1$ is isopropyl, $R_2$ is trifluoromethyl, $R_3$ is chlorine, $R_4$ is hydrogen and X is $X_8$;
h) $R_1$ is isopropyl, $R_2$ is trifluoromethyl, $R_3$ is methyl, $R_4$ is hydrogen and X is $X_8$;
i) $R_1$ is methyl, $R_2$ is bromine, $R_3$ is methyl, $R_4$ is CN and X is $X_1$;
j) $R_1$ is methyl, $R_2$ is bromine, $R_3$ is methyl, $R_4$ is Cl and X is $X_1$;
and (B8) glyphosate+TX, a compound of formula V+TX

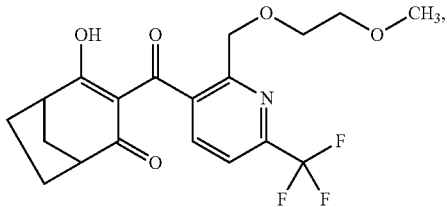 (V)

fomesafen+TX, and (B9) Isopyrazam+TX, Sedaxane+TX, a compound of formula (VI)+TX

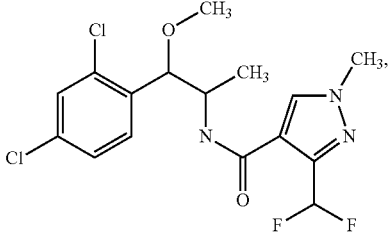 (VI)

a compound of formula (VII)+TX

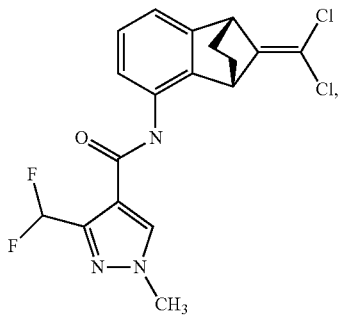 (VII)

Preferred compositions comprising a compound of formula TX and (B) a compound selected from the group consisting of (B1) a strobilurin fungicide+TX, (B2) an azole fungicide+TX, (B3) a morpholine fungicide+TX, (B4) an anilinopyrimidine fungicide+TX, (B5) a fungicide selected from the group consisting of anilazine (878)+TX, arsenates+TX, benalaxyl (56)+TX, benalaxyl-M+TX, benodanil (896)+TX, benomyl (62)+TX, benthiavalicarb+TX, benthiavalicarb-isopropyl (68)+TX, biphenyl (81)+TX, bitertanol (84)+TX, blasticidin-S (85)+TX, bordeaux mixture (87)+TX, boscalid (88)+TX, bupirimate (98)+TX, cadmium chloride+TX, captafol (113)+TX, captan (114)+TX, carbendazim (116)+TX, carbon disulfide (945)+TX, carboxin (120)+TX, carpropamid (122)+TX, cedar leaf oil+TX, chinomethionat (126)+TX, chlorine+TX, chloroneb (139)+TX, chlorothalonil (142)+TX, chlozolinate (149)+TX, cinnamaldehyde+TX, copper+TX, copper ammoniumcarbonate+TX, copper hydroxide (169)+TX, copper octanoate (170)+TX, copper oleate+TX, copper sulphate (87)+TX, cyazofamid (185)+TX, cycloheximide (1022)+TX, cymoxanil (200)+TX, dichlofluanid (230)+TX, dichlone (1052)+TX, dichloropropene (233)+TX, diclocymet (237)+TX, diclomezine (239)+TX, dicloran (240)+TX, diethofencarb (245)+TX, diflumetorim (253)+TX, dimethirimol (1082)+TX, dimethomorph (263)+TX, dinocap (270)+TX, dithianon (279)+TX, dodine (289)+TX, edifenphos (290)+TX, ethaboxam (304)+TX, ethirimol (1133)+TX, etridiazole (321)+TX, famoxadone (322)+TX, fenamidone (325)+TX, fenaminosulf (1144)+TX, fenamiphos (326)+TX, fenarimol (327)+TX, fenfuram (333)+TX, fenhexamid (334)+TX, fenoxanil (338)+TX, fenpiclonil (341)+TX, fentin acetate (347)+TX, fentin chloride+TX, fentin hydroxide (347)+TX, ferbam (350)+TX, ferimzone (351)+TX, fluazinam (363)+TX, fludioxonil (368)+TX, flusulfamide (394)+TX, flutolanil (396)+TX, folpet (400)+TX, formaldehyde (404)+TX, fosetyl-aluminium (407)+TX, fthalide (643)+TX, fuberidazole (419)+TX, furalaxyl (410)+TX, furametpyr (411)+TX, flyodin (1205)+TX, fuazatine (422)+TX, hexachlorobenzene (434)+TX, hymexazole+TX, iminoctadine (459)+TX, iodocarb (3-Iodo-2-propynyl butyl carbamate)+TX, iprobenfos (IBP) (469)+TX, iprodione (470)+TX, iprovalicarb (471)+TX, isoprothiolane (474)+TX, kasugamycin (483)+TX, mancozeb (496)+TX, maneb (497)+TX, manganous dimethyldithiocarbamate+TX, mefenoxam (Metalaxyl-M) (517)+TX, mepronil (510)+TX, mercuric chloride (511)+TX, mercury+TX, metalaxyl (516)+TX, methasulfocarb (528)+TX, metiram (546)+TX, metrafenone+TX, nabam (566)+TX, neem oil (hydrophobic extract)+TX, nuarimol (587)+TX, octhilinone (590)+TX, ofurace (592)+TX, oxadixyl (601)+TX, oxine copper (605)+TX, oxolinic acid (606)+TX, oxycarboxin (608)+TX, oxytetracycline (611)+TX, paclobutrazole (612)+TX, paraffin oil (628)+TX, paraformaldehyde+TX, pencycuron (620)+TX, pentachloronitrobenzene (716)+TX, pentachlorophenol (623)+TX, penthiopyrad+TX, perfurazoate+TX, phosphoric acid+TX, polyoxin (654)+TX, polyoxin D zinc salt (654)+TX, potassium bicarbonate+TX, probenazole (658)+TX, procymidone (660)+TX, propamocarb (668)+TX, propineb (676)+TX, proquinazid (682)+TX, prothiocarb (1361)+TX, pyrazophos (693)+TX, pyrifenox (703)+TX, pyroquilon (710)+TX, quinoxyfen (715)+TX, quintozene (PCNB) (716)+TX, silthiofam (729)+TX, sodium bicarbonate+TX, sodium diacetate+TX, sodium propionate+TX, streptomycin (744)+TX, sulphur (754)+TX, TCMTB+TX, tecloftalam+TX, tecnazene (TCNB) (767)+TX, thiabendazole (790)+TX, thifluzamide (796)+TX, thiophanate (1435)+TX, thiophanate-methyl (802)+TX, thiram (804)+TX, tolclofos-methyl (808)+TX, tolylfluanid (810)+TX, triazoxide (821)+TX, trichoderma harzianum (825)+TX, tricyclazole (828)+TX, triforine (838)+TX, triphenyltin hydroxide (347)+TX, validamycin (846)+TX, vinclozolin (849)+TX, zineb (855)+TX, ziram (856)+TX, zoxamide (857)+TX, 1,1-bis(4-chlorophenyl)-2-ethoxyethanol (IUPAC-Name) (910)+TX, 2+TX, 4-dichlorophenyl benzenesulfonate (IUPAC-/Chemical Abstracts-Name) (1059)+TX, 2-fluoro-N-methyl-N-1-naphthylacetamide (IUPAC-Name) (1295)+TX, 4-chlorophenyl phenyl sulfone (IUPAC-Name) (981)+TX, a compound of formula B-5.1+TX (B-5.1)

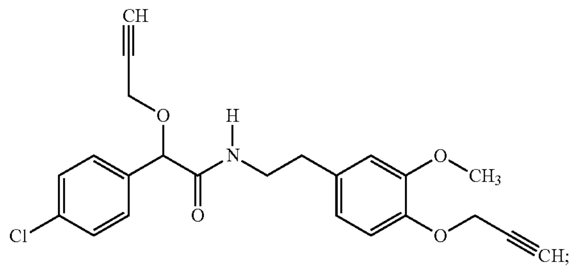

;

a compound of formula B-5.2+TX (B-5.2)

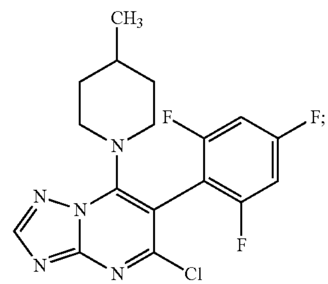

;

a compound of formula B-5.3+TX (B-5.3)

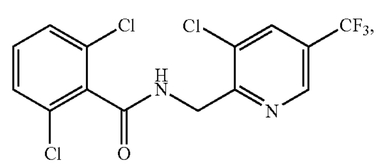

, a compound of formula B-5.4+TX (B-5.4)

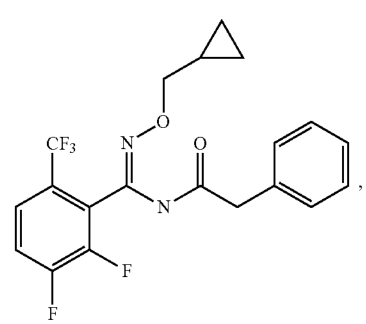

, a compound of formula B-5.5+TX

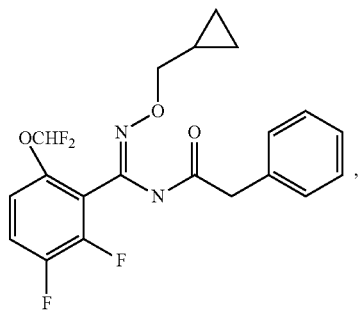

a compound of formula B-5.6+TX

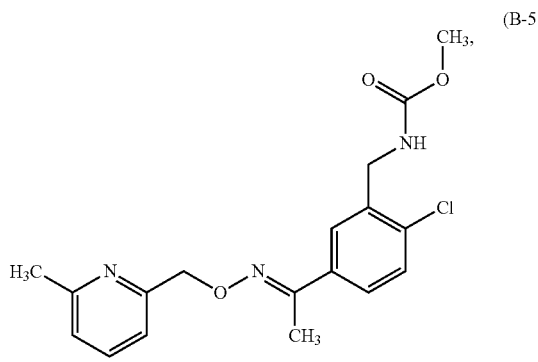

a compound of formula B-5.7+TX

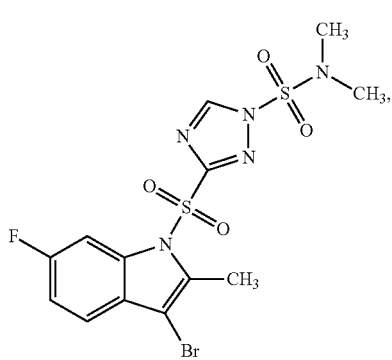

3-difluoromethyl-1-methyl-1H-pyrazole-4-carboxylic acid (2-bicyclopropyl-2-yl-phenyl)-amide (compound B-5.8)+TX, 3-difluoromethyl-1-methyl-1H-pyrazole-4-carboxylic acid (9-isopropyp-1,2,3,4-tetrahydro-1,4-methano-naphthalen-5-yl)-amide (compound B-5.9)+TX, 1,3-dimethyl-5-fluoro-1H-pyrazole-4-carboxylic acid [2-(1,3-dimethylbutyl)phenyl]-amide (compound B-5.10)+TX, 3-difluoromethyl-1-methyl-1H-pyrazole-4-carboxylic acid (3',4'-dichloro-5-fluoro-1,1'-biphenyl-2-yl)-amide (compound B-5.11)+TX, N-{2-[3-chloro-5-(trifluoromethyl)pyridin-2-yl]ethyl}-2-(trifluoromethyl)benzamid (compound B-5.12)+TX, 3-difluoromethyl-1-methyl-1H-pyrazole-4-carboxylic acid N-[2-(1,1,2,2-tetrafluoroethoxy)phenyl]-amide (compound B-5.13)+TX, 3-difluoromethyl-1-methyl-1H-pyrazole-4-carboxylic acid N-[2-(1,1,2,3,3,3-hexafluoropropoxy)phenyl]-amide (compound B-5.14)+TX, 3-difluoromethyl-1-methyl-1H-pyrazole-4-carboxylic acid N-[2-(2-chloro-1,1,2-trifluoroethoxy)phenyl]-amide (compound B-5.15)+TX, 3-difluoromethyl-1-methyl-1H-pyrazole-4-carboxylic acid N-(4'-trifluoromethyl-biphen-2-yl)-amide (compound B-5.16)+TX, 3-difluoromethyl-1-methyl-1H-pyrazole-4-carboxylic acid N-(2'-trifluoromethyl-biphen-2-yl)-amide (compound B-5.17) and 3-difluoromethyl-1-methyl-1H-pyrazole-4-carboxylic acid N-(2'-trifluoromethyl-biphen-2-yl)-amide (compound B-5.18);

(B6) a plant-bioregulator selected from the group consisting of acibenzolar-5-methyl (6)+TX, chlormequat chloride (137)+TX, ethephon (307)+TX, mepiquat chloride (509) and trinexapc-ethyl (841);

(B7) an insecticide selected from the group consisting of abamectin (1)+TX, clothianidin (165)+TX, emamectin benzoate (291)+TX, imidacloprid (458)+TX, tefluthrin (769)+TX, thiamethoxam (792)+TX, a compound of formula B-7.1+TX

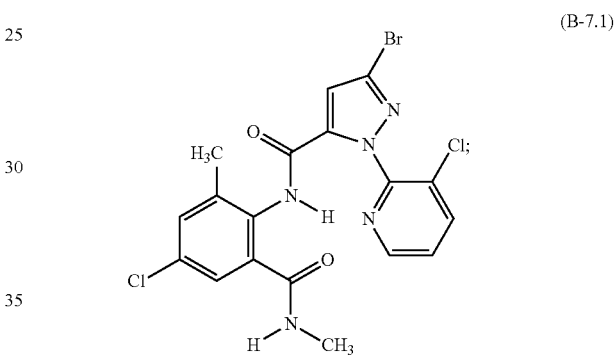

and a compound of formula B-7.2+TX;

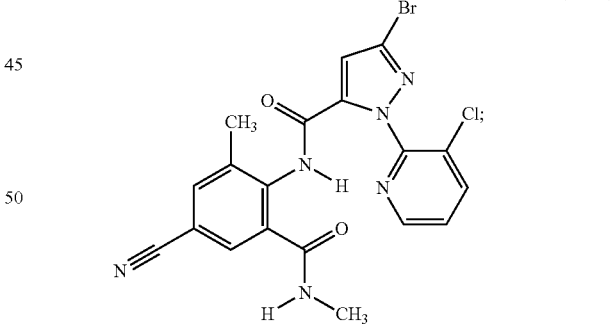

and (B8) glyphosate (419)+TX.

Examples of especially suitable mixtures selected from the following group P:

Group P: Especially Suitable Mixtures According to the Invention:

a strobilurin fungicide selected from azoxystrobin (47)+TX, dimoxystrobin (226)+TX, fluoxastrobin (382)+TX, kresoxim-methyl (485)+TX, metominostrobin (551)+TX, orysastrobin+TX, picoxystrobin (647)+TX, pyraclostrobin (690); trifloxystrobin (832)+TX, a compound of formula B-1.1+TX

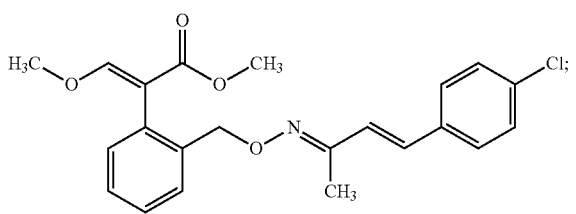
(B-1.1)

an azole fungicide selected from azaconazole (40)+TX, bromuconazole (96)+TX, cyproconazole (207)+TX, difenoconazole (247)+TX, diniconazole (267)+TX, diniconazole-M (267)+TX, epoxiconazole (298)+TX, fenbuconazole (329)+TX, fluquinconazole (385)+TX, flusilazole (393)+TX, flutriafol (397)+TX, hexaconazole (435)+TX, imazalil (449)+TX, imibenconazole (457)+TX, ipconazole (468)+TX, metconazole (525)+TX, myclobutanil (564)+TX, oxpoconazole (607)+TX, pefurazoate (618)+TX, penconazole (619)+TX, prochloraz (659)+TX, propiconazole (675)+TX, prothioconazole (685)+TX, simeconazole (731)+TX, tebuconazole (761)+TX, tetraconazole (778)+TX, triadimefon (814)+TX, triadimenol (815)+TX, triflumizole (834)+TX, triticonazole (842)+TX, diclobutrazol (1068)+TX, etaconazole (1129)+TX, furconazole (1198)+TX, furconazole-cis (1199) and quinconazole (1378);
a morpholine fungicide mixture selected from aldimorph+TX, dodemorph (288)+TX, fenpropimorph (344)+TX, tridemorph (830)+TX, fenpropidin (343)+TX, spiroxamine (740)+TX, piperalin (648) and a compound of formula B-3.1+TX

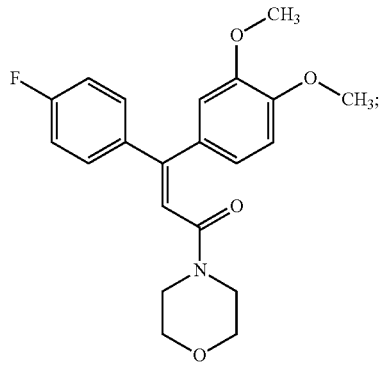
(B-3.1)

an anilino-pyrimidine fungicide selected from cyprodinil (208)+TX, mepanipyrim (508) and pyrimethanil (705);
a fungicide mixture selected from the group consisting of anilazine (878)+TX, arsenates+TX, benalaxyl (56)+TX, benalaxyl-M+TX, benodanil (896)+TX, benomyl (62)+TX, benthiavalicarb+TX, benthiavalicarb-isopropyl (68)+TX, biphenyl (81)+TX, bitertanol (84)+TX, blasticidin-S (85)+TX, bordeaux mixture (87)+TX, boscalid (88)+TX, bupirimate (98)+TX, cadmium chloride+TX, captafol (113)+TX, captan (114)+TX, carbendazim (116)+TX, carbon disulfide (945)+TX, carboxin (120)+TX, carpropamid (122)+TX, cedar leaf oil+TX, chinomethionat (126)+TX, chlorine+TX, chloroneb (139)+TX, chlorothalonil (142)+TX, chlozolinate (149)+TX, cinnamaldehyde+TX, copper+TX, copper ammoniumcarbonate+TX, copper hydroxide (169)+TX, copper octanoate (170)+TX, copper oleate+TX, copper sulphate (87)+TX, cyazofamid (185)+TX, cycloheximide (1022)+TX, cymoxanil (200)+TX, dichlofluanid (230)+TX, dichlone (1052)+TX, dichloropropene (233)+TX, diclocymet (237)+TX, diclomezine (239)+TX, dicloran (240)+TX, diethofencarb (245)+TX, diflumetorim (253)+TX, dimethirimol (1082)+TX, dimethomorph (263)+TX, dinocap (270)+TX, dithianon (279)+TX, dodine (289)+TX, edifenphos (290)+TX, ethaboxam (304)+TX, ethirimol (1133)+TX, etridiazole (321)+TX, famoxadone (322)+TX, fenamidone (325)+TX, fenaminosulf (1144)+TX, fenamiphos (326)+TX, fenarimol (327)+TX, fenfuram (333)+TX, fenhexamid (334)+TX, fenoxanil (338)+TX, fenpiclonil (341)+TX, fentin acetate (347)+TX, fentin chloride+TX, fentin hydroxide (347)+TX, ferbam (350)+TX, ferimzone (351)+TX, fluazinam (363)+TX, fludioxonil (368)+TX, flusulfamide (394)+TX, flutolanil (396)+TX, folpet (400)+TX, formaldehyde (404)+TX, fosetyl-aluminium (407)+TX, fthalide (643)+TX, fuberidazole (419)+TX, furalaxyl (410)+TX, furametpyr (411)+TX, flyodin (1205)+TX, fuazatine (422)+TX, hexachlorobenzene (434)+TX, hymexazole+TX, iminoctadine (459)+TX, iodocarb (3-Iodo-2-propynyl butyl carbamate)+TX, iprobenfos (IBP) (469)+TX, iprodione (470)+TX, iprovalicarb (471)+TX, isoprothiolane (474)+TX, kasugamycin (483)+TX, mancozeb (496)+TX, maneb (497)+TX, manganous dimethyldithiocarbamate+TX, mefenoxam (Metalaxyl-M) (517)+TX, mepronil (510)+TX, mercuric chloride (511)+TX, mercury+TX, metalaxyl (516)+TX, methasulfocarb (528)+TX, metiram (546)+TX, metrafenone+TX, nabam (566)+TX, neem oil (hydrophobic extract)+TX, nuarimol (587)+TX, octhilinone (590)+TX, ofurace (592)+TX, oxadixyl (601)+TX, oxine copper (605)+TX, oxolinic acid (606)+TX, oxycarboxin (608)+TX, oxytetracycline (611)+TX, paclobutrazole (612)+TX, paraffin oil (628)+TX, paraformaldehyde+TX, pencycuron (620)+TX, pentachloronitrobenzene (716)+TX, pentachlorophenol (623)+TX, penthiopyrad+TX, perfurazoate+TX, phosphoric acid+TX, polyoxin (654)+TX, polyoxin D zinc salt (654)+TX, potassium bicarbonate+TX, probenazole (658)+TX, procymidone (660)+TX, propamocarb (668)+TX, propineb (676)+TX, proquinazid (682)+TX, prothiocarb (1361)+TX, pyrazophos (693)+TX, pyrifenox (703)+TX, pyroquilon (710)+TX, quinoxyfen (715)+TX, quintozene (PCNB) (716)+TX, silthiofam (729)+TX, sodium bicarbonate+TX, sodium diacetate+TX, sodium propionate+TX, streptomycin (744)+TX, sulphur (754)+TX, TCMTB+TX, tecloftalam+TX, tecnazene (TCNB) (767)+TX, thiabendazole (790)+TX, thifluzamide (796)+TX, thiophanate (1435)+TX, thiophanate-methyl (802)+TX, thiram (804)+TX, tolclofos-methyl (808)+TX, tolylfluanid (810)+TX, triazoxide (821)+TX, trichoderma harzianum (825)+TX, tricyclazole (828)+TX, triforine (838)+TX, triphenyltin hydroxide (347)+TX, validamycin (846)+TX, vinclozolin (849)+TX, zineb (855)+TX, ziram (856)+TX, zoxamide (857)+TX, 1+TX, 1-bis(4-chlorophenyl)-2-ethoxyethanol (IUPAC-Name) (910)+TX, 2+TX, 4-dichlorophenyl benzenesulfonate (IUPAC-/Chemical Abstracts-Name) (1059)+TX, 2-fluoro-N-methyl-N-1-naphthylacetamide (IUPAC-Name) (1295)+TX, 4-chlorophenyl phenyl sulfone (IUPAC-Name) (981)+TX,
a compound of formula B-5.1+TX, a compound of formula B-5.2+TX, a compound of formula B-5.3+TX, a compound of formula B-5.4+TX, a compound of formula B-5.5+TX, a compound of formula B-5.6+TX, a compound of formula B-5.7+TX, compound B-5.8+TX, compound B-5.9+TX, compound B-5.10+TX, compound B-5.11+TX, compound B-5.12+TX, compound B-5.13+TX, compound B-5.14+TX, compound B-5.15+TX, compound B-5.16+TX, compound B-5.17 and compound B-5.18;

a plant-bioregulator selected from the group consisting of acibenzolar-S-methyl (6)+TX, chlormequat chloride (137)+TX, ethephon (307)+TX, mepiquat chloride (509) and trinexapc-ethyl (841);
an insecticide selected from the group consisting of abamectin (1)+TX, clothianidin (165)+TX, emamectin benzoate (291)+TX, imidacloprid (458)+TX, tefluthrin (769)+TX, thiamethoxam (792)+TX, and glyphosate (419)+TX, a compound of formula V)+TX

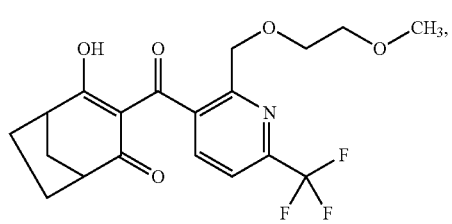

(V)

fomesafen+TX, and (B9) Isopyrazam+TX, Sedaxane+TX, a compound of formula (VI)+TX

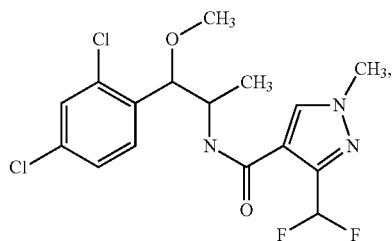

(VI)

a compound of formula (VII)+TX

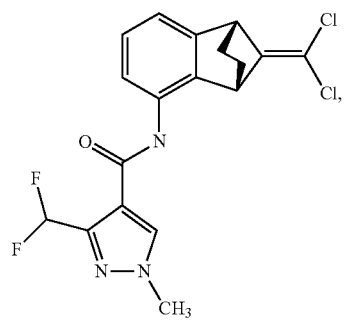

(VII)

Further examples of especially suitable mixtures selected from the following group Q:
Group Q: Especially Suitable Compositions According to the Invention:
a strobilurin fungicide selected from the group consisting of azoxystrobin+TX, dimoxystrobin+TX, fluoxastrobin+TX, kresoxim-methyl+TX, metominostrobin+TX, orysastrobin+TX, picoxystrobin+TX, pyraclostrobin; trifloxystrobin and a compound of formula B-1.1;
an azole fungicide selected from the group consisting of azaconazole+TX, bromuconazole+TX, cyproconazole+TX, difenoconazole+TX, diniconazole+TX, diniconazole-M+TX, epoxiconazole+TX, fenbuconazole+TX, fluquinconazole+TX, flusilazole+TX, flutriafol+TX, hexaconazole+TX, imazalil+TX, imibenconazole+TX, ipconazole+TX, metconazole+TX, myclobutanil+TX, oxpoconazole+TX, pefurazoate+TX, penconazole+TX, prochloraz+TX, propiconazole+TX, prothioconazole+TX, simeconazole+TX, tebuconazole+TX, tetraconazole+TX, triadimefon+TX, triadimenol+TX, triflumizole+TX, triticonazole+TX, diclobutrazol+TX, etaconazole+TX, furconazole+TX, furconazole-cis and quinconazole;
a morpholine fungicide selected from the group consisting of aldimorph+TX, dodemorph+TX, fenpropimorph+TX, tridemorph+TX, fenpropidin+TX, spiroxamine+TX, piperalin and a compound of formula B-3.1;
an anilino-pyrimidine fungicide selected from the group consisting of cyprodinil+TX, mepanipyrim and pyrimethanil;
a fungicide selected from the group consisting of benalaxyl+TX, benalaxyl-M+TX, benomyl+TX, bitertanol+TX, boscalid+TX, captan+TX, carboxin+TX, carpropamid+TX, chlorothalonil+TX, copper+TX, cyazofamid+TX, cymoxanil+TX, diethofencarb+TX, dithianon+TX, famoxadone+TX, fenamidone+TX, fenhexamide+TX, fenoxycarb+TX, fenpiclonil+TX, fluazinam+TX, fludioxonil+TX, flutolanil+TX, folpet+TX, guazatine+TX, hymexazole+TX, iprodione+TX, lufenuron+TX, mancozeb+TX, metalaxyl+TX, mefenoxam+TX, metrafenone+TX, nuarimol+TX, paclobutrazol+TX, pencycuron+TX, penthiopyrad+TX, procymidone+TX, proquinazid+TX, pyroquilon+TX, quinoxyfen+TX, silthiofam+TX, sulfur+TX, thiabendazole+TX, thiram+TX, triazoxide+TX, tricyclazole+TX, a compound of formula B-5.1+TX, a compound of formula B-5.2+TX, a compound of formula B-5.3+TX, a compound of formula B-5.4+TX, a compound of formula B-5.5+TX, a compound of formula B-5.6+TX, a compound of formula B-5.7+TX, a compound of formula B-5.8+TX, a compound of formula B-5.9+TX, a compound of formula B-5.10 and a compound of formula B-5.12;
a plant-bioregulator selected from acibenzolar-S-methyl+TX, chlormequat chloride+TX, ethephon+TX, mepiquat chloride and trinexapc-ethyl;
an insecticide selected from abamectin+TX, emamectin benzoate+TX, tefluthrin+TX, thiamethoxam+TX, and glyphosate+TX, a compound of formula V

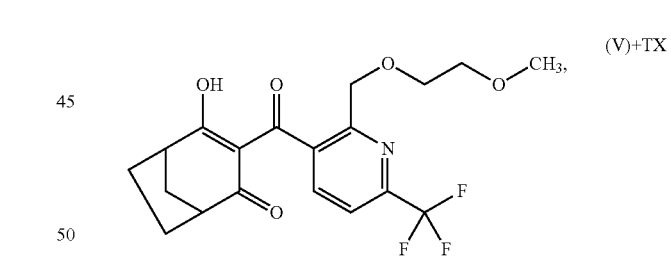

(V)+TX fomesafen+TX, and (B9) Isopyrazam+TX, Sedaxane+TX, a compound of formula (VI)+TX

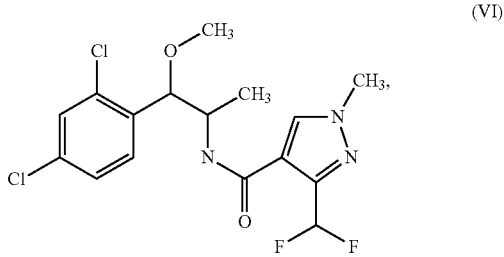 [SMILES: COC(c1ccc(Cl)cc1Cl)C(C)NC(=O)c1cn(C)nc1C(F)F]

(VI)

a compound of formula (VII)+TX

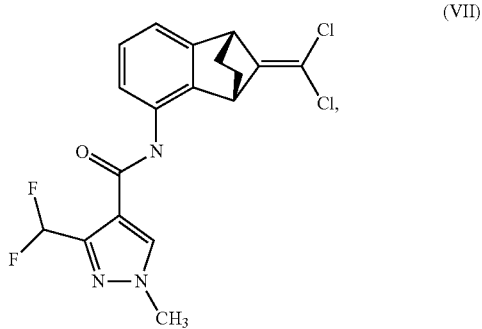 [SMILES: Cn1cc(C(=O)Nc2cccc3c2[C@@H]2CC[C@H]3C2=C(Cl)Cl)c(C(F)F)n1]

(VII)

It has been found that the use of component (B) in combination with component TX surprisingly and substantially may enhance the effectiveness of the latter against fungi, and vice versa. Additionally, the method of the invention is effective against a wider spectrum of such fungi that can be combated with the active ingredients of this method, when used solely.

In general, the weight ratio of component TX to component (B) is from 2000:1 to 1:1000. A non-limiting example for such weight ratios is compound of formula I: compound of formula B-2 is 10:1. The weight ratio of component TX to component (B) is preferably from 100:1 to 1:100; more preferably from 20:1 to 1:50.

The active ingredient mixture of component TX to component (B) comprises compounds of formula I and a further, other biocidally active ingredients or compositions or if desired, a solid or liquid adjuvant preferably in a mixing ratio of from 1000:1 to 1:1000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

It has been found, surprisingly, that certain weight ratios of component TX to component (B) are able to give rise to synergistic activity. Therefore, a further aspect of the invention are compositions, wherein component TX and component (B) are present in the composition in amounts producing a synergistic effect. This synergistic activity is apparent from the fact that the fungicidal activity of the composition comprising component TX and component (B) is greater than the sum of the fungicidal activities of component TX and of component (B). This synergistic activity extends the range of action of component TX and component (B) in two ways. Firstly, the rates of application of component TX and component (B) are lowered whilst the action remains equally good, meaning that the active ingredient mixture still achieves a high degree of phytopathogen control even where the two individual components have become totally ineffective in such a low application rate range. Secondly, there is a substantial broadening of the spectrum of phytopathogens that can be controlled.

A synergistic effect exists whenever the action of an active ingredient combination is greater than the sum of the actions of the individual components. The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):
ppm=milligrams of active ingredient (=a.i.) per liter of spray mixture
X=% action by active ingredient A) using p ppm of active ingredient
Y=% action by active ingredient B) using q ppm of active ingredient.

According to COLBY, the expected (additive) action of active ingredients A)+B) using p+q ppm of active ingredient is $$E = X + Y - \frac{X \cdot Y}{100}$$

If the action actually observed (O) is greater than the expected action (E), then the action of the combination is super-additive, i.e. there is a synergistic effect. In mathematical terms, synergism corresponds to a positive value for the difference of (O-E). In the case of purely complementary addition of activities (expected activity), said difference (O-E) is zero. A negative value of said difference (O-E) signals a loss of activity compared to the expected activity.

However, besides the actual synergistic action with respect to fungicidal activity, the compositions according to the invention can also have further surprising advantageous properties. Examples of such advantageous properties that may be mentioned are: more advantageous degradability; improved toxicological and/or ecotoxicological behaviour; or improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination.

Some compositions according to the invention have a systemic action and can be used as foliar, soil and seed treatment fungicides.

With the compositions according to the invention it is possible to inhibit or destroy the phytopathogenic microorganisms which occur in plants or in parts of plants (fruit, blossoms, leaves, stems, tubers, roots) in different useful plants, while at the same time the parts of plants which grow later are also protected from attack by phytopathogenic microorganisms.

The compositions according to the invention can be applied to the phytopathogenic microorganisms, the useful plants, the locus thereof, the propagation material thereof, storage goods or technical materials threatened by microorganism attack.

The compositions according to the invention may be applied before or after infection of the useful plants, the propagation material thereof, storage goods or technical materials by the microorganisms.

A further aspect of the present invention is a method of controlling diseases on useful plants or on propagation material thereof caused by phytopathogens, which comprises applying to the useful plants, the locus thereof or propagation material thereof a composition according to the invention. Preferred is a method, which comprises applying to the useful plants or to the locus thereof a composition according to the invention, more preferably to the useful plants. Further preferred is a method, which comprises applying to the propagation material of the useful plants a composition according to the invention.

The components (B) are known. Where the components (B) are included in "The Pesticide Manual" [The Pesticide Manual—A World Compendium; Thirteenth Edition; Editor: C. D. S. Tomlin; The British Crop Protection Council], they are described therein under the entry number given in round brackets hereinabove for the particular component (B); for example, the compound "abamectin" is described under entry number (1). Most of the components (B) are referred to hereinabove by a so-called "common name", the relevant "ISO common name" or another "common name" being used in individual cases. If the designation is not a "common name", the nature of the designation used instead is given in round brackets for the particular component (B); in that case, the IUPAC name, the IUPAC/Chemical Abstracts name, a "chemical name", a "traditional name", a "compound name" or a "development code" is used or, if neither one of those designations nor a "common name" is used, an "alternative name" is employed.

The following components B) are registered under a CAS-Reg. No.
aldimorph (CAS 91315-15-0); arsenates (CAS 1327-53-3); benalaxyl-M (CAS 98243-83-5); benthiavalicarb (CAS 413615-35-7); cadmium chloride (CAS 10108-64-2); cedar leaf oil (CAS 8007-20-3); chlorine (CAS 7782-50-5); cinnamaldehyde (CAS: 104-55-2); copper ammoniumcarbonate (CAS 33113-08-5); copper oleate (CAS 1120-44-1); iodocarb (3-Iodo-2-propynyl butyl carbamate) (CAS 55406-53-6); hymexazole (CAS 10004-44-1); manganous dimethyldithiocarbamate (CAS 15339-36-3); mercury (CAS 7487-94-7; 21908-53-2; 7546-30-7); metrafenone (CAS 220899-03-6); neem oil (hydrophobic extract) (CAS 8002-65-1); orysastrobin CAS 248593-16-0); paraformaldehyde (CAS 30525-89-4); penthiopyrad (CAS 183675-82-3); phosphoric acid (CAS 7664-38-2); potassium bicarbonate (CAS 298-14-6); sodium bicarbonate (CAS 144-55-8); sodium diacetate (CAS 127-09-3); sodium propionate (CAS 137-40-6); TCMTB (CAS 21564-17-0); and tolylfluanid (CAS 731-27-1). Compound B-1.1 ("enestrobin") is described in EP-0-936-213; compound B-3.1 ("flumorph") in U.S. Pat. No. 6,020,332, CN-1-167-568, CN-1-155-977 and in EP-0-860-438; compound B-5.1 ("mandipropamid") in WO 01/87822; compound B-5.2 in WO 98/46607; compound B-5.3 ("fluopicolide") in WO 99/42447; compound B-5.4 ("cyflufenamid") in WO 96/19442; compound B-5.5 in WO 99/14187; compound B-5.6 ("pyribencarb") is registered under CAS-Reg. No. 325156-49-8; compound B-5.7 ("amisulbrom" or "ambromdole") is registered under CAS-Reg. No. 348635-87-0; compound B-5.8 (3-difluoromethyl-1-methyl-1H-pyrazole-4-carboxylic acid (2-bicyclopropyl-2-yl-phenyl)-amide) is described in WO 03/74491; compound B-5.9 (3-difluoromethyl-1-methyl-1H-pyrazole-4-carboxylic acid (9-isopropyp-1,2,3,4-tetrahydro-1,4-methano-naphthalen-5-yl)-amide) is described in WO 04/35589 and in WO 06/37632; compound B-5.10 (1,3-dimethyl-5-fluoro-1H-pyrazole-4-carboxylic acid [2-(1,3-dimethylbutyl)phenyl]-amide) is described in WO 03/10149; compound B-5.11 (3-difluoromethyl-1-methyl-1H-pyrazole-4-carboxylic acid (3',4'-dichloro-5-fluoro-1,1'-biphenyl-2-yl)-amide; "bixafen") is registered under CAS-Reg. No.: 581809-46-3 and described in WO 03/70705; compound B-5.12 (N-{2-[3-Chloro-5-(trifluoromethyl)pyridin-2-yl]ethyl}-2-(trifluoromethyl)benzamid; "fluopyram") is registered under CAS-Reg. No: 658066-35-4 and described in WO 04/16088; compounds B-5.13, B-5.14 and B-5.15 are described in WO 2007/17450; compounds B-5.16, B-5.17 and B-5.18 are described in WO 2006/120219; The compounds of formula IV are for example described in WO 04/067528, WO 2005/085234, WO 2006/111341, WO 03/015519, WO 2007/020050, WO 2006/040113, and WO 2007/093402. The compound of formula V is described in WO 2001/094339. Isopyraxam (3-(difluoromethyl)-1-methyl-N-[1,2,3,4-tetrahydro-9-(1-methylethyl)-1,4-methanonaphthalen-5-yl]-1H-pyrazole-4-carboxamide) is described in WO 2004/035589, in WO 2006/037632 and in EP1556385B1 and is registered under the CAS-Reg. 881685-58-1. Sedaxane (N-[2-[1,1'-bicyclopropyl]-2-ylphenyl]-3-(difluoromethyl)-1-methyl-1H-pyrazole-4-carboxamide) is described in WO 2003/074491 and is registered under the CAS-Reg. 874967-67-6; The compound of formula (VI) is described in WO 2008/014870; and the compounds of formula (VII) is described in WO 2007/048556. Fomesafen is registered under the CAS-Reg. No. 72178-02-0.

Throughout this document the expression "composition" stands for the various mixtures or combinations of components TX and (B), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the components TX and (B) is not essential for working the present invention.

The compositions according to the invention may also comprise more than one of the active components (B), if, for example, a broadening of the spectrum of disease control is desired. For instance, it may be advantageous in the agricultural practice to combine two or three components (B) with component TX. An example is a composition comprising a compound of formula (I), azoxystrobin and cyproconazole.

Controlling or preventing means reducing the infestation of crop plants or of non-living materials by phytopathogenic or spoilage microorganisms or organisms potentially harmful to man, especially fungal organisms, to such a level that an improvement is demonstrated.

Furthermore, the compounds of formula (I) of the present invention may find use as plant growth regulators or in plant health applications.

Plant growth regulators (PGRs) are generally any substances or mixtures of substances intended to accelerate or retard the rate of growth or maturation, or otherwise alter the development of plants or their produce.

Plant growth regulators (PGRs) affect growth and differentiation of plants.

More specifically, various plant growth regulators (PGRs) can, for example, reduce plant height, stimulate seed germination, induce flowering, darken leaf coloring, change the rate of plant growth and modify the timing and efficiency of fruiting.

Plant health applications include, for example, improvement of advantageous properties/crop characteristics including: emergence, crop yields, protein content, increased vigour, faster maturation, increased speed of seed emergence, improved nitrogen utilization efficiency, improved water use efficiency, improved oil content and for quality, improved digestibility, faster ripening, improved flavor, improved starch content, more developed root system (improved root growth), improved stress tolerance (e.g. against drought, heat, salt, light, UV, water, cold), reduced ethylene (reduced production and/or inhibition of reception), tillering increase, increase in plant height, bigger leaf blade, less dead basal leaves, stronger tillers, greener leaf color, pigment content, photosynthetic activity, less input needed (such as fertilizers or water), less seeds needed, more productive tillers, earlier flowering, early grain maturity, less plant verse (lodging), increased shoot growth, enhanced plant vigor, increased plant stand and early and better germination.

Advantageous properties, obtained especially from treaded seeds, are e.g. improved germination and field establishment, better vigor, more homogeneous field establishment.

Advantageous properties, obtained especially from foliar and/or in-furrow application are e.g. improved plant growth and plant development, better growth, more tillers, greener leafes, largers leaves, more biomass, better roots, improved stress tolerance of the plants, more grain yield, more biomass harvested, improved quality of the harvest (content of fatty acids, metabolites, oil etc), more marketable products (e.g. improved size), improved process (e.g. longer shelf-life, better extraction of compounds), improved quality of seeds (for being seeded in the following seasons for seed production); or any other advantages familiar to a person skilled in the art.

The term plant health thus comprises various sorts of improvements of plants that are not connected to the control of harmful microbes, harmful microorganism (which causes disease), harmful germs or harmful fungi (which causes disease).

Table 1 below illustrates examples of individual compounds of formula (I) and intermediate (I.3) according to the invention.

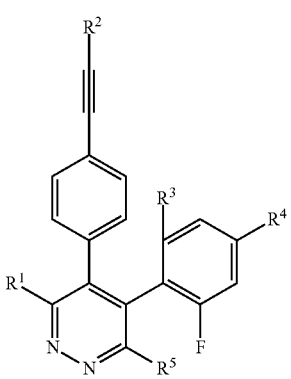

(I)

| Compound No. | R¹ | R² | R³ | R⁴ | R⁵ |
|---|---|---|---|---|---|
| 1 (I.3) | CH₃ | H | F | F | OH |
| 2 | CH₃ | H | F | F | Cl |
| 3 | CH₃ | H | F | OCH₃ | Cl |
| 4 | CH₃ | H | F | OCH₃ | OCH₃ |
| 5 | CH₃ | H | F | F | OCH₃ |
| 6 | CH₃ | Cl | F | F | Cl |
| 7 | CH₃ | Cl | F | OCH₃ | Cl |
| 8 | CH₃ | Cl | F | OCH₃ | OCH₃ |
| 9 | CH₃ | H | Cl | F | Cl |
| 10 | CH₃ | H | Cl | F | OCH₃ |
| 11 | CH₃ | H | Cl | OCH₃ | Cl |
| 12 | CH₃ | H | Cl | OCH₃ | OCH₃ |
| 13 | CH₃ | Cl | F | F | OCH₃ |
| 14 | CH₃ | Cl | Cl | F | Cl |
| 15 | CH₃ | Cl | Cl | F | OCH₃ |

-continued

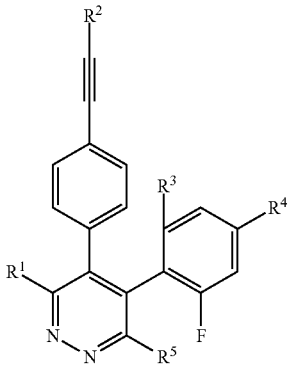

(I)

| Compound No. | R¹ | R² | R³ | R⁴ | R⁵ |
|---|---|---|---|---|---|
| 16 | CH₃ | Cl | Cl | OCH₃ | Cl |
| 17 | CH₃ | Cl | Cl | OCH₃ | OCH₃ |

The following non-limiting example illustrates the above-described invention in more detail.

EXAMPLE 1

This Example Illustrates the Preparation of 3-chloro-5-(4-ethynylphenyl)-6-methyl-4-(2,4,6-trifluorophenyl)pyridazine (Compound No. 2)

a) Preparation of 1-(4-trimethylsilanylethynylphenyl)propan-1-one

A mixture of 1.74 g 4'-bromopropiophenone, 2.0 g ethynyltrimethylsilane, 260 mg bis(triphenylphosphine)palladium(II) dichloride, 260 mg copper(I) iodide and 15 ml diisopropylamine in 40 ml tetrahydrofuran is heated at reflux for 1 h. After cooling the reaction mixture is diluted with water and extracted with ethyl acetate. The combined organic layer is washed with brine, dried over sodium sulfate and evaporated under reduced pressure. The residue is purified by chromatography on silica gel, using a mixture of heptane/ethyl acetate 9:1 as eluent to obtain 1-(4-trimethylsilanylethynylphenyl)propan-1-one, m.p. 36-37° C.

b) Preparation of 2-bromo-1-(4-trimethylsilanylethynylphenyl)propan-1-one

Bromine (8.4 g) is slowly added to 1-(4-trimethylsilanylethynylphenyl)propan-1-one (10.0 g) in 100 ml of tetrahydrofuran at 0° C. and subsequently stirred at room temperature for 2 h. The reaction mixture is diluted with water and extracted with ethyl acetate. The organic layer is washed with brine, dried over sodium sulfate and concentrated under reduced pressure. The remainder is purified by chromatography on silica gel, using a mixture of heptane/ethyl acetate 19:1 as eluent to obtain 2-bromo-1-(4-trimethylsilanylethynylphenyl)propan-1-one as a yellow solid.

c) Preparation of 4-(4-ethynylphenyl)-5-hydroxy-5-methyl-3-(2,4,6-trifluorophenyl)-5H-furan-2-one Triethylamine (0.72 g) is slowly added to a solution of 2-bromo-1-(4-trimethylsilanylethynyl-phenyl)propan-1-one (1.76 g), 2,4,6-trifluorophenylacetic acid (1.35 g) in 50 ml of acetonitrile and this mixture is stirred for 16 h at room temperature. Subsequently 1,8-diazabicyclo-[5.4.0]undec-7-ene (DBU, 2.36 g) is slowly added under cooling and stirring is continued for 1 h. Then air is blown through the reaction mixture for 1 h. The reaction mixture is poured into an aqueous ammonium chloride solution and the mixture is extracted with ethyl acetate. The combined organic layer is washed with brine, dried over sodium sulfate and evaporated under reduced pressure. The remainder is purified by chromatography on silica gel, using a mixture of heptane/ethyl acetate 3:1 as eluent to obtain 4-(4-ethynylphenyl)-5-hydroxy-5-methyl-3-(2,4,6-trifluorophenyl)-5H-furan-2-one as a yellowish foam.

d) Preparation of 5-(4-ethynylphenyl)-6-methyl-4-(2,4,6-trifluorophenyl)-2H-pyridazin-3-one (Compound No. 1)

Hydrazine hydrate (0.17 g) is added to a solution of 0.87 g 4-(4-ethynylphenyl)-5-hydroxy-5-methyl-3-(2,4,6-trifluorophenyl)-5H-furan-2-one in 5 ml of 1-butanol and this mixture is heated for 4 h to 120° C. The reaction mixture is evaporated under reduced pressure and the residue is purified by chromatography on silica gel, using a mixture of toluene/ethyl acetate 5:1 as eluent to obtain 5-(4-ethynylphenyl)-6-methyl-4-(2,4,6-trifluorophenyl)-2H-pyridazin-3-one (Compound No. 1) as colourless crystals, m.p. 252-254° C.

e) A mixture of 5-(4-ethynylphenyl)-6-methyl-4-(2,4,6-trifluorophenyl)-2H-pyridazin-3-one (Compound No. 1, 0.4 g) and 5 ml of phosphorus oxychloride is heated at 110° C. for 2 h. After cooling the reaction mixture is evaporated under reduced pressure. The remainder is taken up with ethyl acetate and water and the phases are separated. The organic layer is washed with water and brine, dried over sodium sulfate and evaporated under reduced pressure. The residue is purified by chromatography on silica gel, using a mixture of heptane/ethyl acetate 4:1 as eluent to obtain 3-chloro-5-(4-ethynylphenyl)-6-methyl-4-(2,4,6-trifluorophenyl)pyridazine (Compound No. 2) as colourless crystals, m.p. 174-175° C.

EXAMPLE 2

This Example Illustrates the Preparation of 4-(2,6-difluoro-4-methoxyphenyl)-5-(4-ethynylphenyl)-3-methoxy-6-methylpyridazine (Compound No. 4)

A mixture of 3-chloro-5-(4-ethynylphenyl)-6-methyl-4-(2,4,6-trifluorophenyl)pyridazine (Compound No. 2, 1.0 g), sodium methoxide (30% solution in methanol, 1.78 g) and 20 ml of tetrahydrofuran is heated to 55° C. for 2 h. Subsequently the reaction mixture is cooled, diluted with water and extracted with ethyl acetate. The combined organic layer is washed with water and brine, dried over sodium sulfate and evaporated under reduced pressure. The residue is purified by chromatography on silica gel, using a mixture of heptane/ethyl acetate 2:1 as eluent to obtain 4-(2,6-difluoro-4-methoxyphenyl)-5-(4-ethynylphenyl)-3-methoxy-6-methylpyridazine (Compound No. 4) as colourless crystals, m.p. 192-193° C.

BIOLOGICAL EXAMPLES

*Alternaria Solani*/Tomato/Preventative (Action Against *Alternaria* on Tomato)
4-week old tomato plants cv. Roter Gnom were treated with the formulated test compound in a spray chamber. The test plants were inoculated by spraying them with a spore suspension two days after application. The inoculated test plants were incubated at 22/18° C. (day/night) and 95% rh in a greenhouse and the percentage leaf area covered by disease was assessed when an appropriate level of disease appears on untreated check plants (5 to 7 days after application).
Compounds 2 and 4 according to the invention at 200 ppm inhibited fungal infestation in this test to at least 80%, while under the same conditions untreated control plants are infected by the phytopathogenic fungi to over 80%.
*Botryotinia fuckeliana* (*Botrytis cinerea*)/Tomato/Preventative (Action Against *Botrytis* on Tomato)
4-week old tomato plants cv. Roter Gnom were treated with the formulated test compound in a spray chamber. The test plants were inoculated by spraying them with a spore suspension two days after application. The inoculated test plants were incubated at 20° C. and 95% rh in a greenhouse and the percentage leaf area covered by disease is assessed when an appropriate level of disease appears on untreated check plants (5 to 6 days after application).
Compounds 2 and 4 according to the invention at 200 ppm inhibited fungal infestation in this test to at least 80%, while under the same conditions untreated control plants are infected by the phytopathogenic fungi to over 80%.
*Erysiphe necator* (*Uncinula necator*)/Grape/Preventative (Action Against Powdery Mildew on Grape)
5-week old grape seedlings cv. Gutedel were treated with the formulated test compound in a spray chamber. The test plants are inoculated by shaking plants infected with grape powdery mildew above them 1 day after application. The inoculated test plants were incubated at 24/22° C. (day/night) and 70% rh under a light regime of 14/10 h (light/dark) and the percentage leaf area covered by disease was assessed when an appropriate level of disease appears on untreated check plants (7 to 9 days after application).
Compound 2 according to the invention at 200 ppm inhibited fungal infestation in this test to at least 80%, while under the same conditions untreated control plants are infected by the phytopathogenic fungi to over 80%.
*Magnaporthe grisea* (*Pyricularia oryzae*)/Rice/Preventative (Action Against Rice Blast)
3-week old rice plants cv. Koshihikari were treated with the formulated test compound in a spray chamber. The test plants were inoculated by spraying them with a spore suspension two days after application. The inoculated test plants were incubated at 25° C. and 95% rh and the percentage leaf area covered by disease was assessed when an appropriate level of disease appears on untreated check plants (7 to 9 days after application).
Compounds 2 and 4 according to the invention at 200 ppm inhibited fungal infestation in this test to at least 80%, while under the same conditions untreated control plants are infected by the phytopathogenic fungi to over 80%.
*Mycosphaerella graminicola* (*Septoria tritici*)/Wheat/Preventive (Action Against *Septoria* Leaf Spot on Wheat)
2-week old wheat plants cv. Riband were treated with the formulated test compound in a spray chamber. The test plants were inoculated by spraying a spore suspension on them one day after application. After an incubation period of 1 day at 22° C./21° C. (day/night) and 95% rh, the test plants were kept at 22° C./21° C. (day/night) and 70% rh in a greenhouse. The percentage leaf area covered by disease is assessed when an appropriate level of disease appears on untreated check plants (16 to 19 days after application).
Compounds 2 and 4 according to the invention at 200 ppm inhibited fungal infestation in this test to at least 80%, while under the same conditions untreated control plants are infected by the phytopathogenic fungi to over 80%.

*Mycosphaerella graminicola* (*Septoria tritici*)/Wheat/Curative (Action Against *Septoria* Leaf Spot on Wheat)

2-week old wheat plants cv. Riband are inoculated by spraying them with a spore suspension. After an incubation period of 2 days at 22° C./21° C. (day/night) and 95% rh, the test plants are kept at 22° C./21° C. (day/night) and 70% rh in a climate chamber. The inoculated test plants are treated with the formulated test compound in a spray chamber 5 days after inoculation. The percentage leaf area covered by disease is assessed when an appropriate level of disease appears on untreated check plants (11 to 14 days after application).

Compounds 2 and 4 according to the invention at 200 ppm inhibited fungal infestation in this test to at least 80%, while under the same conditions untreated control plants are infected by the phytopathogenic fungi to over 80%.

*Puccinia recondita*/Wheat/Preventative (Action Against Brown Rust on Wheat)

2-week old wheat plants cv. Arina were treated with the formulated test compound in a spray chamber. The test plants were inoculated by spraying them with a spore suspension one day after application. After an incubation period of 1 day at 20° C. and 95% rh, the test plants were kept at 20° C./18° C. (day/night) and 60% rh in a greenhouse. The percentage leaf area covered by disease was assessed when an appropriate level of disease appears on untreated check plants (12 to 14 days after application).

Compound 2 according to the invention at 200 ppm inhibited fungal infestation in this test to at least 80%, while under the same conditions untreated control plants are infected by the phytopathogenic fungi to over 80%.

*Pyrenophora teres* (*Helminthosporium teres*)/Barley/Preventative (Action Against Net Blotch on Barley)

1-week old barley plants cv. Regina were treated with the formulated test compound in a spray chamber. The test plants were inoculated by spraying them with a spore suspension 2 days after application. The inoculated test plants were incubated at 20° C. and 95% rh and the percentage leaf area covered by disease was assessed when an appropriate level of disease appears on untreated check plants (5 to 7 days after application).

Compounds 2 and 4 according to the invention at 200 ppm inhibited fungal infestation in this test to at least 80%, while under the same conditions untreated control plants are infected by the phytopathogenic fungi to over 80%.

The invention claimed is:

1. A compound of formula (I)

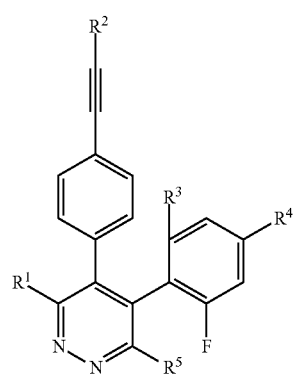

(I)

wherein
$R^1$ is methyl or ethyl;
$R^2$ is H or chloro;
$R^3$ is fluoro or chloro;
$R^4$ is fluoro or methoxy; and
$R^5$ is chloro or methoxy;
or an agrochemically usable salt form thereof.

2. A compound according to claim 1 wherein
$R^1$ is methyl;
$R^2$ is H;
$R^3$ is fluoro;
$R^4$ is fluoro or methoxy; and
$R^5$ is chloro.

3. A compound according to claim 1 selected from 3-chloro-5-(4-ethynylphenyl)-6-methyl-4-(2,4,6-trifluorophenyl)pyridazine; 3-chloro-4-(2,6-difluoro-4-methoxyphenyl)-5-(4-ethynylphenyl)-6-methylpyridazine; 4-(2,6-difluoro-4-methoxyphenyl)-5-(4-ethynylphenyl)-3-methoxy-6-methylpyridazine; 4-(4-ethynylphenyl)-6-methoxy-3-methyl-5-(2,4,6-trifluorophenyl)pyridazine; 3-chloro-5-(4-chloroethynylphenyl)-6-methyl-4-(2,4,6-trifluorophenyl)pyridazine; and 3-chloro-5-(4-chloroethynylphenyl)-4-(2,6-difluoro-4-methoxyphenyl)-6-methylpyridazine.

4. A fungicidal composition for controlling or protecting against phytopathogenic microorganisms, comprising as active ingredient at least one compound as defined in claim 1, in free form or in agrochemically usable salt form, and at least one adjuvant.

5. A composition according to claim 4 which further comprises at least one additional fungicidally active compound, preferably selected from the group consisting of azoles, pyrimidinyl carbinoles, 2-amino-pyrimidines, morpholines, anilinopyrimidines, pyrroles, phenylamides, benzimidazoles, dicarboximides, carboxamides, strobilurines, dithiocarbamates, N-halomethylthiotetrahydrophthalimides, copper-compounds, nitrophenols, organo-phosphorus-derivatives, pyridazines, triazolopyrimidines, carboxamides and benzamides.

6. A method of controlling an infestation of crop plants, harvested food crops or non-living materials by phytopathogenic or spoilage microorganisms or organisms potentially harmful to man, which comprises the application of a compound as defined in claim 1, as active ingredient to the plant, to parts of the plants or to the locus thereof, to seeds or to any part of the non-living materials.

7. A method according to claim 6 wherein the control is via curative application.

8. A method according to claim 6 wherein the pathogenic microorganism is a fungal organism.

9. A method according to claim 6 wherein the fungal organism is selected from *Alternaria solani, Botryotinia fuckeliana, Erysiphe necator, Magnaporthe grisea, Mycosphaerella graminicola, Puccinia recondite* and *Pyrenophora teres*.

10. A method according to claim 9 wherein the fungal organism is *Mycosphaerella graminicola*.

11. A process for the preparation of a compound of formula (I.1)

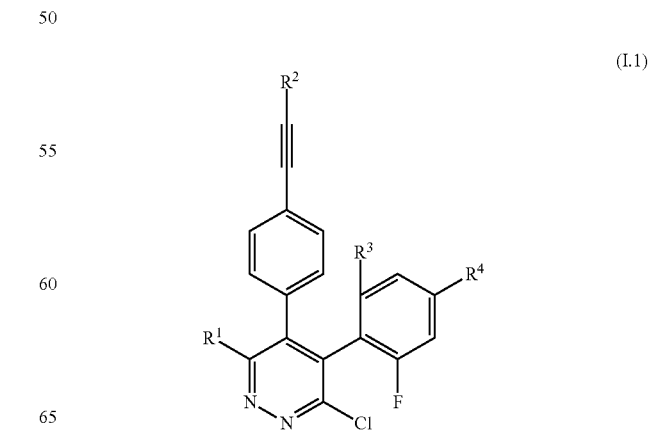

(I.1)

which comprises reacting a compound of formula (I.3)

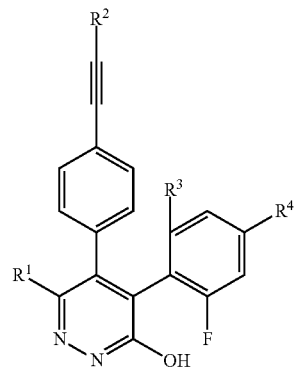
(I.3)

with phosphorous oxychloride or thionyl chloride;

wherein the compound of formula (I.3) is optionally prepared by reacting a compound of formula (II)

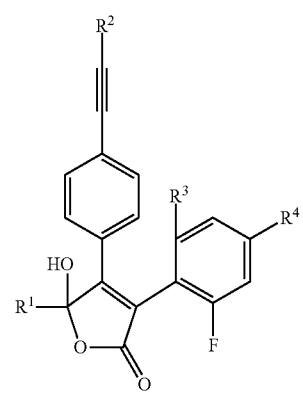
(II)

with a hydrazine derivative;

wherein the compound of formula (II) is optionally prepared by reacting a compound of formula (III)

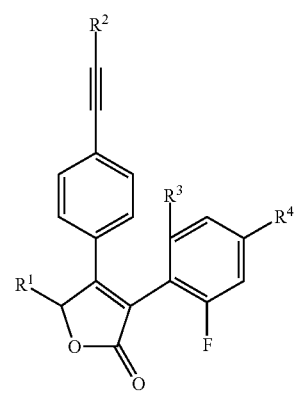
(III)

with oxygen, air, or 3-chloroperbenzoic acid;

wherein the compound of formula (III) is optionally prepared by reacting a compound of formula (IV)

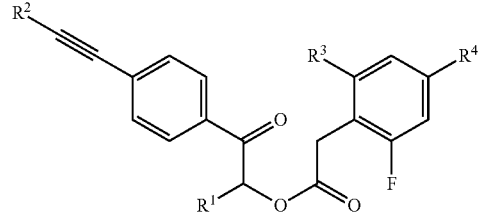
(IV)

with a base;
wherein $R^1$, $R^2$, $R^3$ and $R^4$ are as defined in claim 1.

12. A compound selected from (I.3), (II), (III) and (IV)

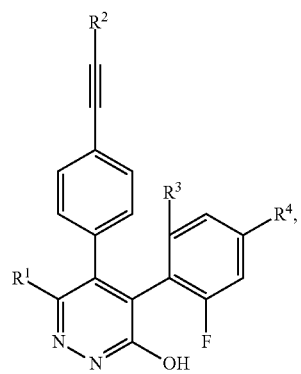
(I.3)

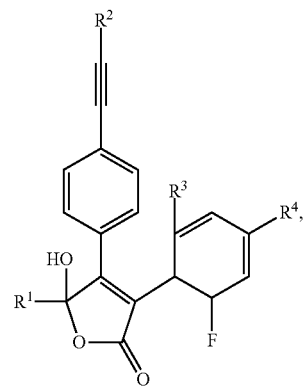
(II)

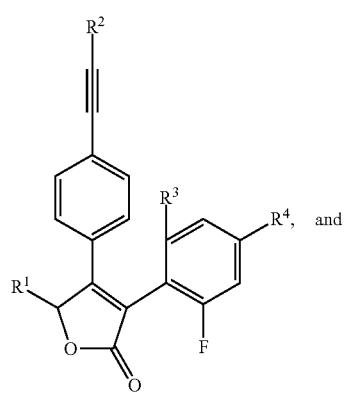
(III)

(IV)
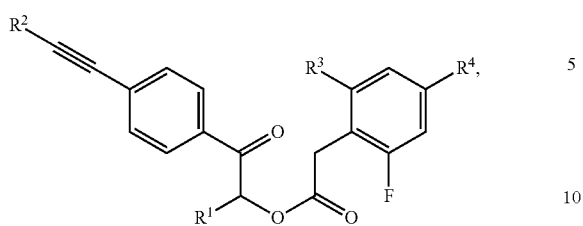
wherein R¹, R², R³ and R⁴ are as defined in claim 1.
* * * * *